(12) United States Patent
Utz

(10) Patent No.: US 12,201,807 B2
(45) Date of Patent: Jan. 21, 2025

(54) MEDICAL INFUSION PUMP TREATMENT IDENTIFICATION

(71) Applicant: CHS HEALTHCARE VENTURES, INC., Decatur, GA (US)

(72) Inventor: Hans Utz, Decatur, GA (US)

(73) Assignee: CHS HEALTHCARE VENTURES, INC., Decatur, GA (US)

( * ) Notice: Subject to any disclaimer, the term of this patent is extended or adjusted under 35 U.S.C. 154(b) by 926 days.

(21) Appl. No.: 17/231,360

(22) Filed: Apr. 15, 2021

(65) Prior Publication Data

US 2021/0228796 A1 Jul. 29, 2021

Related U.S. Application Data

(63) Continuation of application No. 16/548,347, filed on Aug. 22, 2019, now Pat. No. 11,007,315.

(51) Int. Cl.
*A61M 5/14* (2006.01)
*A61M 5/142* (2006.01)
*A61M 5/168* (2006.01)
*A61M 5/172* (2006.01)
*G16H 20/17* (2018.01)

(52) U.S. Cl.
CPC ........ *A61M 5/142* (2013.01); *A61M 5/16827* (2013.01); *A61M 5/172* (2013.01); *A61M 5/1415* (2013.01); *A61M 2005/14208* (2013.01); *A61M 5/16877* (2013.01); *A61M 2205/587* (2013.01); *A61M 2205/6009* (2013.01); *A61M 2205/6063* (2013.01); *G16H 20/17* (2018.01)

(58) Field of Classification Search
CPC .. A61M 5/142; A61M 5/16827; A61M 5/172; A61M 5/1415; A61M 5/16877; A61M 2005/14208; A61M 2205/587; A61M 2205/6009; A61M 2205/6063; A61M 2205/3592; G16H 20/17; G16H 40/40; G16H 40/63
See application file for complete search history.

(56) References Cited

U.S. PATENT DOCUMENTS

| 5,041,086 A | 8/1991 | Koening et al. |
| 5,423,750 A | 8/1995 | Spiller |
| 5,681,285 A | 10/1997 | Ford et al. |

(Continued)

FOREIGN PATENT DOCUMENTS

| AU | 2007282071 | 2/2008 |
| CN | 102847204 | 9/2012 |

(Continued)

*Primary Examiner* — Amber R Stiles
(74) *Attorney, Agent, or Firm* — Bryan L. Baysinger; Maynard Nexsen PC

(57) ABSTRACT

Disclosed are various embodiments for identification of medical fluid treatment to a medical patient. Systems and their operations are disclosed to identify a fluidic treatment protocol among a plurality of medical infusion lines. The system includes medical infusion pumps, illuminating medical infusion lines, and computing resources to initiate identification. Fluidic medical treatment is prone to error, cognitive load is elevated in healthcare operations, the various embodiments disclosed herein are systems and methods to decrease error and reduce cognitive load by identifying as a visual cue the medical fluid treatment protocol.

13 Claims, 12 Drawing Sheets

(56) References Cited

U.S. PATENT DOCUMENTS

| | | | |
|---|---|---|---|
| 6,059,768 A | 5/2000 | Friedman | |
| 7,860,583 B2 | 12/2010 | Condurso et al. | |
| 8,679,075 B2 | 3/2014 | Lurvey et al. | |
| 9,501,619 B2 | 11/2016 | Portnoy et al. | |
| 10,232,107 B2 | 3/2019 | Utz | |
| 2007/0106263 A1 | 5/2007 | Ward | |
| 2010/0006171 A1 | 1/2010 | Tomlin et al. | |
| 2011/0196306 A1* | 8/2011 | De La Huerga | A61M 5/16827 604/93.01 |
| 2011/0264463 A1 | 10/2011 | Kincaid et al. | |
| 2011/0282160 A1* | 11/2011 | Bhadri | A61B 1/313 600/236 |
| 2013/0123579 A1* | 5/2013 | Adams | A61B 90/92 600/117 |
| 2014/0330205 A1 | 11/2014 | Tian | |
| 2016/0175521 A1 | 6/2016 | Adams et al. | |
| 2017/0014023 A1 | 1/2017 | Kern | |
| 2017/0021095 A1 | 1/2017 | Utz | |
| 2017/0023216 A1 | 1/2017 | Utz | |
| 2017/0258983 A1 | 9/2017 | Utz | |
| 2017/0340815 A1 | 11/2017 | Utz | |
| 2017/0281855 A1 | 12/2017 | Utz | |
| 2018/0177938 A1 | 6/2018 | Provost et al. | |
| 2019/0091398 A1 | 3/2019 | Utz | |
| 2019/0217006 A1* | 7/2019 | Anand | A61M 39/08 |

FOREIGN PATENT DOCUMENTS

| | | |
|---|---|---|
| EP | 1157711 | 5/2008 |
| EP | 2009533 | 12/2008 |
| WO | 2019164988 A | 8/2019 |

\* cited by examiner

MEDICAL INFUSION PUMP TREATMENT IDENTIFICATION

CROSS-REFERENCE TO RELATED APPLICATION

This application is a continuation of and claims the benefit and priority of U.S. patent application Ser. No. 16/548,347 filed on Aug. 22, 2019, entitled "FLUIDIC MEDICAL TREATMENT IDENTIFICATION" the contents of which is herein incorporated by reference in its entirety.

FIELD

The present invention relates to medical tubing and medical infusion pump technology. More specifically, the application of technology to medical tubing and medical infusion pumps for the identification of a fluidic medical treatment.

BACKGROUND

Fluidic medical treatment protocols or plans, also known as medical fluid treatments, are utilized in a variety of medical environments. A few examples include the critical care unit ('CCU'), the specialty care unit ('SCU'), the medication care unit ('MCU'), and the oncology care unit ('OCU'). Medical fluid treatment is often conducted utilizing a medical infusion pump. The medical infusion pump will have medical infusion lines attached to the syringe mechanisms of the medical infusion pump. The medical infusion lines often run to a manifold, and from the manifold to the patient receiving medical fluid treatment. The medical infusion lines often have inline components such as filters, ports, roller clamps for regulation, back check valves, drip chambers, and more.

In a given medical fluid treatment environment, a patient can experience a plurality of medical infusion lines running from multiple medical infusion pumps. These lines carry a variety of fluidic medical compounds that encompass a medical fluid treatment plan. These compounds have specific administration requirements and the specific route the medical fluid treatment travels is tailored to the medical fluid treatment plan.

Distinguishing between multiple infusion lines is a difficult task that is placed in an atmosphere of high stress and rapid timing. The medical industry refers to the atmosphere as placing a high cognitive load on practitioners. This high cognitive load can lead to medication delivery error as a result of improperly distinguishing one medical infusion line from another. Arguably, the confusion of one medical infusion line from another is one of the leading causes of preventable medication error. As a result of the difficulties in distinguishing between multiple medical infusion lines and their associated fluid sources and outputs, as well as the potentially life-threatening possibilities that can occur if incompatible medications are injected through the same medical infusion line; there is a need for accurate identification of medical infusion lines.

BRIEF DESCRIPTION OF THE DRAWINGS

Many aspects of the present disclosure can be better understood with reference to the following drawings. The components in the drawings are not necessarily to scale, with emphasis instead being placed upon clearly illustrating the principles of the disclosure. Moreover, in the drawings, like reference numerals designate corresponding parts throughout the several views.

DETAILED DESCRIPTION

Figure 1:
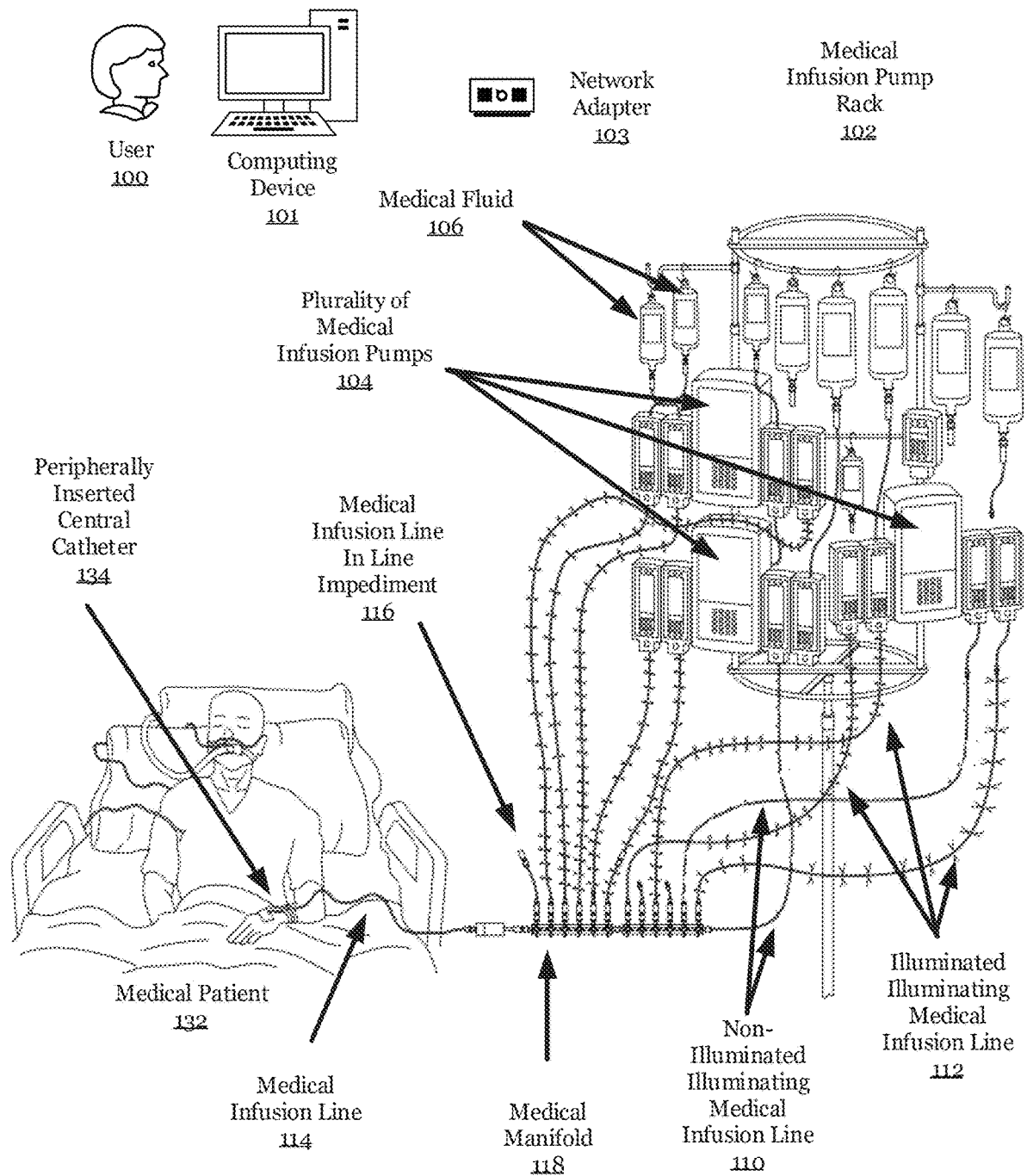
FIG. 1 is a schematic diagram of a medical infusion pump system administering a medical fluid treatment in a first embodiment of the present disclosure.

Systems and methods for identification of a medical fluid treatment with a medical fluid pump and illuminating medical fluid lines are disclosed. In the following discussion, a general description of the system and its components is provided, followed by a discussion of the operation of the same.

Medical fluid treatments are commonly categorized as colloids and crystalloids. Colloid solutions contain large molecules that cannot pass through semi-permeable membranes and are used to expand intravascular volume by drawing fluid from extravascular space through high osmotic pressure. Examples of colloid solutions include albumin, dextrans, and hydroxyethyl starches. Crystalloid solutions contain solutes such as electrolytes or dextrose, which are easily mixed and dissolvable in solution. Crystalloids contain small molecules that flow easily across semi permeable membranes, which allows for transfer from the bloodstream into the cells and tissue. Crystalloids may increase fluid volume in interstitial and intravascular space. Examples of crystalloid solutions include isotonic, hypotonic, and hypertonic solutions.

Isotonic solutions have an osmolality of 250 to 375 mOsm/L. Isotonic solutions have the same osmotic pressure as plasma, creating constant pressure inside and outside the cells, which causes the cells to remain the same and does not cause any fluid shifts within compartments. Isotonic solutions are useful to increase intravascular volume and are utilized to treat vomiting, diarrhea, shock, metabolic acidosis, and for resuscitation purposes and the administration of blood and blood products.

Hypotonic solutions have a lower concentration, or tonicity, of solutes and have an osmolality equal to or less than 250 mOsm/L. The infusion of hypotonic solutions lowers the osmolality within the vascular space and causes fluid to shift to the intracellular and interstitial space. Cells will swell but may also delete fluid within the vascular space.

Hypertonic solutions have a higher concentration, or tonicity, of solutes and have an osmolality equal to or greater than 375 mOsm/L. The osmotic pressure gradient draws water out of the intracellular space into the extracellular space.

Primary medical infusion lines are used to infuse continuous or intermittent fluids or medications. They may consist of additional parts. For example, a backcheck valve may be in place to prevent fluid or medication from traveling in the wrong direction. Access ports are often found along the medical infusion line to administer secondary medications and to give push medications. Roller clamps are used to regulate the speed of, or to stop or start, a gravity-based infusion. Additionally, secondary medical infusion lines may come from the primary medical infusion lines and may be used to infuse intermittent fluids or medications.

Medical infusion lines require continuous sterile changing. The Center for Disease Control recommends medical infusion lines be changed according to the following timeline. Primary tubing with hypotonic, isotonic, or hypertonic continuous solutions should be changed every 72-96 hours. Secondary or intermittent IV solutions or medications are recommended to be changed every 24 hours. The secondary or intermittent medical infusion lines are often repeatedly connected and disconnected thus raising the issue of contamination and requiring more frequent changing. Infusions containing fat emulsions are recommended to be changed ever 24 hours. Blood products are recommended to be changed every 4 hours or 4 units, whichever comes first. These changes increase the risk of error and lead to confusion in the medical facility operation. The disclosures herein address these risks and provide embodiments to assist in interpreting the change of medical fluid lines.

Focusing now on the example embodiment of FIG. 1. In FIG. 1, a schematic diagram of a medical infusion pump system administering a medical fluid treatment protocol is disclosed. Typical protocols for administering the medical infusion lines, in situations such as the one depicted in FIG. 1, instruct the medical practitioner to physically handle or trace the line from its source all the way to the patient to ensure that the infusion and its delivery are proper. In this example embodiment, a medical infusion pump rack (102) is configured to hold the medical fluid (106) containers and the plurality of medical infusion pumps (104). Medical infusion racks are usually metallic assemblies that hold and maintain the positioning of various objects for medical fluid treatment. In FIG. 1, the medical rack (102) is configured to hold the medical fluid bags (106) as well as the plurality of medical infusion pumps (104). Often times one medical infusion rack may hold several medical infusion pumps at the same time as depicted in FIG. 1. The medical infusion pumps (104) are configured to connect to the illuminating medical infusion lines (110, 112). The illuminating medical infusion lines (110, 112) connect to the medical infusion pumps (104) and terminate in the manifold (118). In other embodiments, the illuminating medical infusion lines terminate at the medical patient (132) and the medical manifold (118) does not exist.

In FIG. 1, the user (100) interacts with the computing device (101). The computing device (101) can be any device capable of receiving instructions from a user and processing those instructions on physical medium. Typical computing devices include personal computers configured with an operating system such as Windows 10®, Google Chrome OS®, or Mac OSX®. Additional embodiments of computing devices include mobile devices and tablets configured with operating systems. A typical tablet device would be a Samsung Galaxy Tablet®, an Apple iPad®, or any other mobile computing device. Further, mobile computing devices include the Apple iPhone® and the Samsung Galaxy®. Many other mobile computing devices are available therefore the description herein is not a limiting factor to the type of mobile computing device.

The computing device (101) is configured to connect through a network adapter (103) to communicate with the plurality of medical infusion pumps (104). The network adapter is configured to communicate through a local area network, a wireless network, and through Bluetooth® protocols. Additional networking embodiments are disclosed herein and contemplated by the present disclosure, including but not limited to cellular, wireless, local, regional, connected, and unconnected networks. The computing device (101) communicating through the network adapter (103) transmits information to and receives information from the plurality of medical infusion pumps (104).

In the example embodiment of FIG. 1, the computing device (101) receives a medical fluid treatment plan from the user (100). The medical fluid treatment plan in the example embodiment is a specific set of medical fluids to be administered to the medical patient (132). The medical fluid treatment plan can include a plan for simply exchanging medical lines after use and expiration. It may also include diagnostic requests of illuminating specific illuminating medical infusion lines. The medical treatment plan in this embodiment is defined broadly as any signal transferred from the computing device (101) to the medical infusion pumps (104) that causes action or inaction from the illuminating medical infusion lines (110, 112).

The non-illuminated illuminating medical infusion line (110) is a medical infusion line with the corresponding illuminating light transmission channel positioned on or near the surface of the fluid transmission channel of the medical infusion line. The illuminated illuminating medical infusion line (112) is a medical infusion line with the corresponding illuminating light transmission channel positioned on or near the surface of the fluid transmission channel of the medical infusion line where it has the light transmission channel illuminating for identification. Example embodiments in FIGS. 4, 5, 11, and 12 add additional disclosure for the light transmission channel and the fluid transmission channel. Correspondingly, the light transmission channel is illuminated when the light transmission channel is exposed to a source of illumination. In this manner, when a source of illumination is applied to the illuminating infusion line, the infusion line illuminates allowing a medical practitioner to more readily identify the infusion line for medical services to the patient. Medical services performed by the medical practitioner can include things such as adjusting the delivery of fluids to the patient, responding to medical alerts on the medical infusion pump, changing the medical infusion line, and any other such operations as will occur to those of skill in the art.

A channel, as that term is used in this specification, means a pathway, passage, medium, or other form of transmission of fluid, light, information, or any other transmittable as will occur to those of skill in the art. In some embodiments, a channel may be implemented as a conduit allowing the transmission of light, for example, an optical fiber for fiber optic light transmission. Another example of a channel, according to embodiments of the present invention, is implemented as a conduit that includes a hollow fluid transmission line allowing for the flow or transmission of fluids through the conduit. Alternatively, a channel may be implemented simply as a medium for transmission. For example, the structure that forms a conduit around a fluid transmission line, as discussed in more detail below, may itself be a channel for transmission of light for illuminating the conduit itself.

The source of illumination is housed within, on the exterior, or near the medical infusion pump and is referred to as an illumination module. The illumination module is a light source that can be constructed out of any variety of light emitting substances, materials, and devices. A source of light may be a laser, a light emitting diode ('LED'), an organic light emitting diode ('OLED'), chemiluminescence, or electroluminescence to name but a few sources of light that would be sufficient to traverse the length of the medical infusion line.

In the example of FIG. 1, the medical manifold (118) terminates into a medical infusion line (114) wherein the medical infusion line terminates at the medical patient (132). In the example embodiment, a peripherally inserted central catheter (134) is disclosed. Additional entry port areas to the medical patient (132) are available and disclosed herein such as peripheral lines, central lines, tunneled lines, implantable ports, and midline catheters to name a few.

In FIG. 1, the user (100) upon querying the medical fluid treatment plan on the computing device (101) transmits the information through the network to the plurality of medical infusion pumps (104). The medical infusion pumps correspondingly illuminate the illuminating medical infusion lines that correspond to the medical fluid treatment plan. The illumination corresponds to the specific medical fluid registered at each of the peristaltic pumps on the medical infusion pumps. The computing device (101) and the medical infusion pumps (104) are capable of bi-directional communications, both transmitting and receiving instructions from the other for identification of the corresponding medical fluid and illumination thereof of the illuminating medical infusion lines that correspond to the medical fluid treatment plan. Further, the computing device (101) and the plurality of medical infusion pumps (104) are capable of illuminating varying illuminating medical infusion lines for diagnostic, identification, servicing, and other responsibilities as deemed by a fluid medical treatment plan. For instance, the changing of medical fluid lines, according to duration of use, is a necessary requirement under the Center for Disease Control. This disclosure aids in the replacement of specific medical fluid infusion lines under designated United States Center for Disease Control protocols.

Figure 2:
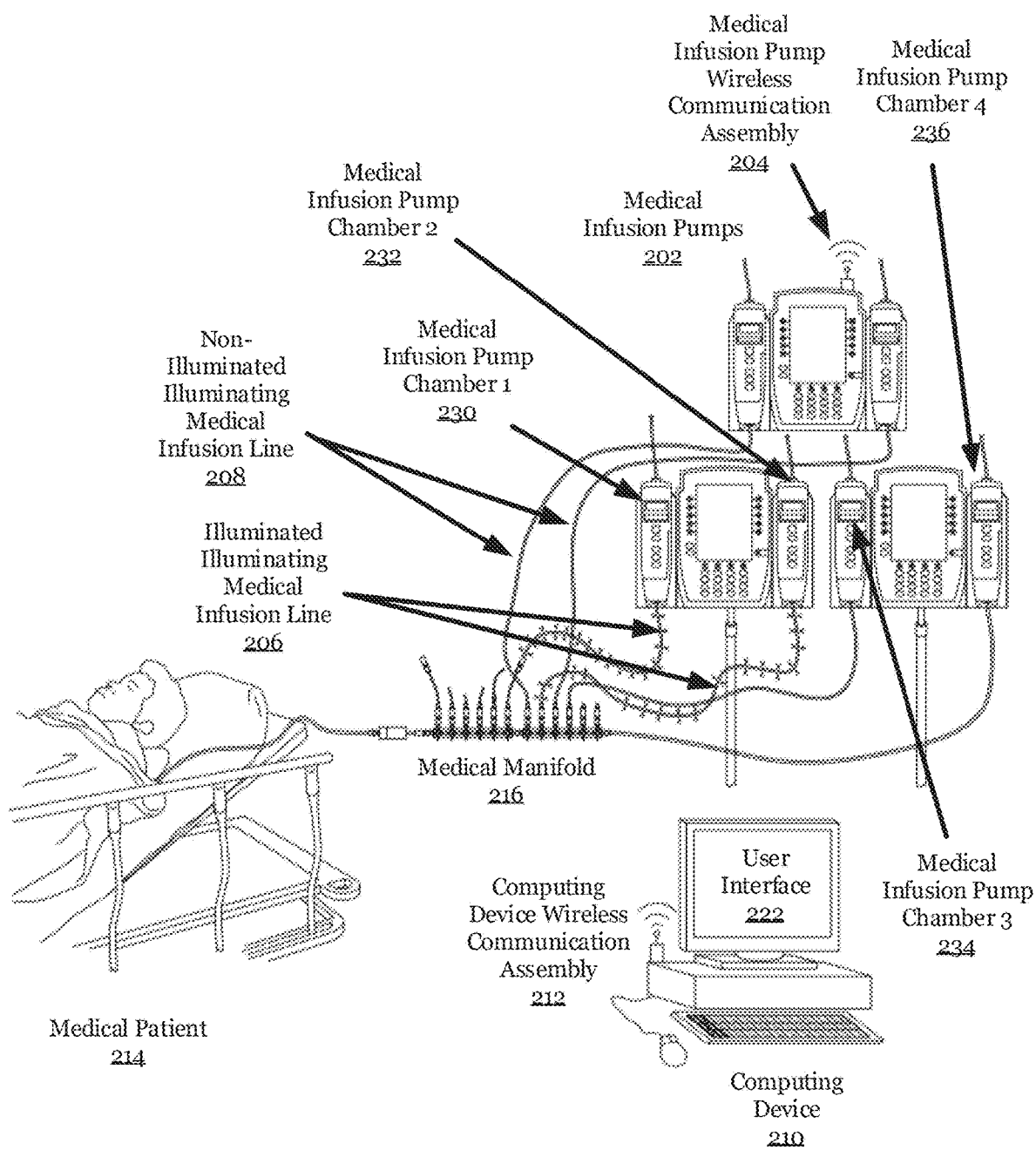
FIG. 2 is a schematic diagram of a medical infusion pump system along with additional technology involved in a medical fluid treatment plan as an additional embodiment of the present disclosure.

In the example embodiment of FIG. 2, a schematic diagram of a medical infusion pump system along with additional technology involved in a medical fluid treatment plan is disclosed. According to the example embodiment, the medical infusion pump (202) is equipped with a medical infusion pump wireless communication assembly (204) for communication with the computing device (210). Additional embodiments include a local area network connection from the computing device (210) to the medical infusion pump (202). Examples of medical infusion pumps include models by manufacturers such as Medtronic®, Smiths Medical®, and Benton Dickinson®. The purpose of the medical infusion pump is to deliver medical fluids into a medical patient's body in a controlled and precise manner. As such, there are many different types of medical infusion pumps and the disclosures herein apply to the variety of medical infusion pumps. For instance, some medical infusion pumps are designed to be stationery at a medical patients bedside table. Others are designed to be portable and wearable to accommodate a variety of environments. Special purpose infusion pumps also exist, such as enteral pumps used to deliver liquid nutrients and medications to a patient's digestive tract. Patient-controlled analgesia pumps, which are used to deliver pain medication, are equipped with a feature that allows patients to self-administer a controlled amount of medication. Insulin pumps, that typically deliver insulin to patients with diabetes, are most often found in a home setting.

Medical infusion pumps according to the disclosure herein may be powered electrically or mechanically or both. For example, a syringe style medical infusion pump holds fluid in a reservoir of a syringe, and a moveable piston controls fluid delivery. In an elastomeric pump, the medical fluid is held in a stretchable balloon reservoir and pressure from the elastic walls of the balloon drives fluid delivery. In a peristaltic pump, a set of rollers pinch down on a length of flexible tubing, thereby pushing the fluid rhythmically forward. In a multi-channel pump, fluids can be delivered from multiple reservoirs at multiple rates. This disclosure includes embodiments of a smart pump that is equipped with the features of an illuminating medical infusion line, along with adaptability and the ability to configure to computing devices that include software defined methodologies and monitoring.

In the example embodiment of FIG. 2, the medical infusion pump (202) receives instructions from the computing device's wireless communication assembly (212) through the medical infusion pump wireless communication assembly (204). These instructions may include the medical fluid treatment plan, diagnostic instructions, operation instructions, and maintenance instructions. In the example embodiment, the instructions received by the medical infusion pump (202) indicate that the medical infusion pump should illuminate the illuminating infusion line attached to the medical infusion pump (202) in the medical infusion pump chamber 1 (230). As a result, the medical infusion line attached to the medical infusion pump (202) and terminating in the medical infusion pump chamber 1 (230) illuminates the illuminating medical infusion line (206). Again, the illuminating infusion line is illuminated for identification of a treatment plan or protocol, a diagnostic reason—such as changing or replacing specific lines, for informational purposes—to identify where each line originates and terminates, and for any other purpose as will be known by those with skill in the art.

In FIG. 2, the medical manifold (216) is equipped to receive the illuminated illuminating medical infusion line (206) along with any non-illuminated illuminating medical infusion lines (208). The medical manifold is a wider chamber or channel into which the smaller illuminating medical infusion lines are connected. In additional embodiments, the medical manifold (216) is absent and the illuminated illuminating medical infusion lines (206) and the non-illuminated medical infusion lines (208) terminate into the medical patient (214).

In the example embodiment of FIG. 2, the computing device (210) is shown with a user interface (222) in which a practitioner can interact with the computing device (210) to perform operations such as a fluid medical treatment plan, a diagnostic test, or identification test on the medical infusion pump (202) to trigger action on behalf of the illuminating medical infusion lines.

In the example embodiment of FIG. 2, disclosed is one illuminating medical infusion line which is illuminated from the signal sent from the computing device (210) to the medical infusion pump (202). In alternative embodiments, the medical infusion pump (202) transmits the signal without the need of the computing device (210). These medical infusion pumps are often referred to as smart pumps, as they are embedded with a special purpose computing device. Therefore, what is also disclosed is the ability to embed the computing device (210) within the medical infusion pump (202) wherein all the functions described by the computing device (210) can be performed from the medical infusion pump (202), often by accessing a user interface directly on or near the medical infusion pump. An interface is not necessary to trigger the signaling of the illuminating medical infusion lines; additional embodiments include a simple trigger or button that can be activated by a computing device or user that transmits a signal to the medical infusion pump (202) to turn on the source of illumination for the illuminating medical infusion line.

Figure 3:
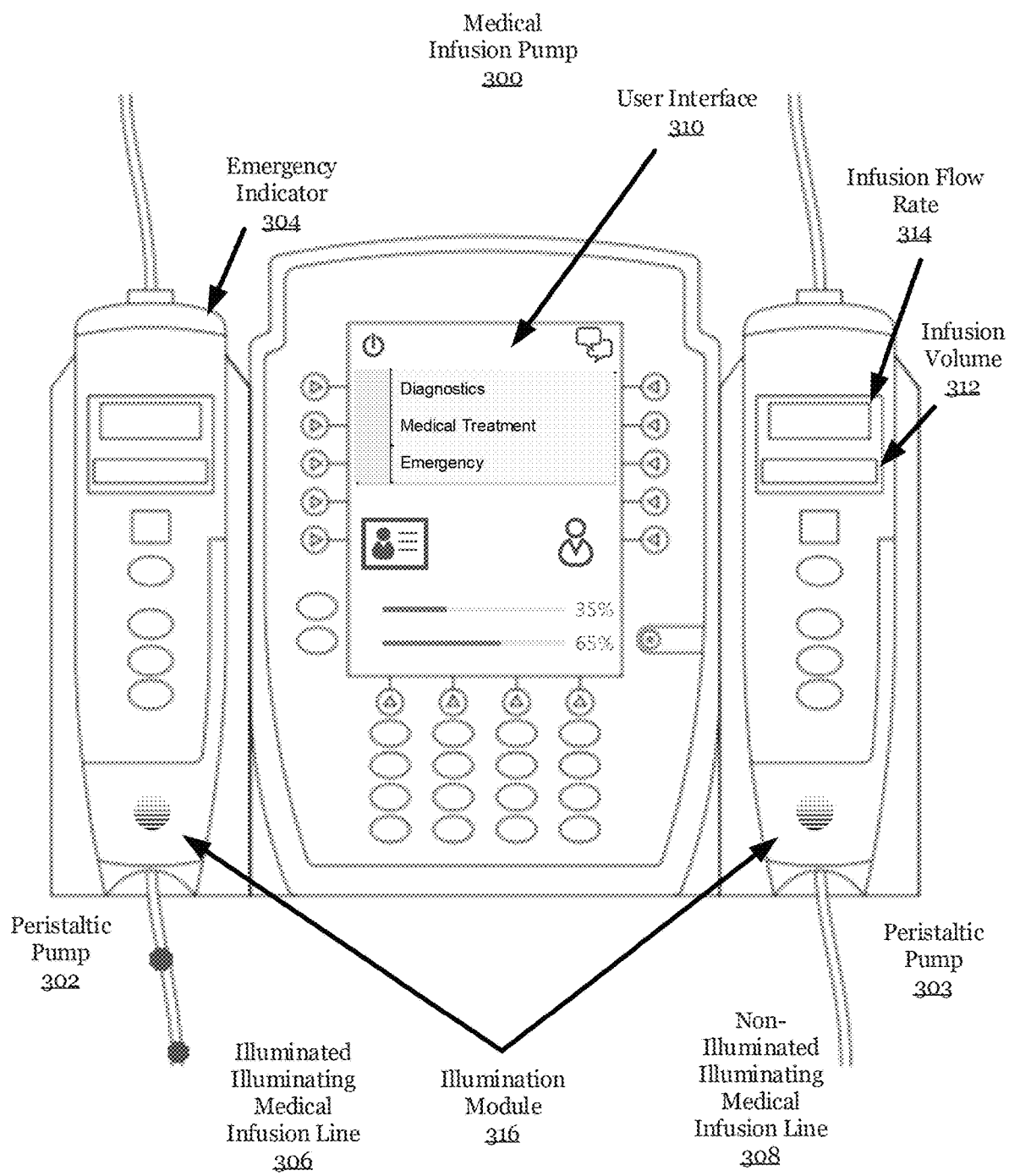
FIG. 3 is a schematic diagram of a medical infusion pump along with a medical infusion pump graphical user interface as an additional embodiment of the present disclosure.

FIG. 3 is an example embodiment of a schematic diagram for a medical infusion pump (300) along with a medical infusion pump user interface (310). Exemplary medical infusion pumps were described previously. This embodiment focuses on the interactive regions of the medical infusion pump (300) and what is termed as a smart pump. The user interface (310) provides a multitude of features and settings that a user may use to further accommodate the use of and treatment with medical fluids. In this embodiment, we focus on the medical infusion pump (300) receiving a signal from a computing device. The received signal can be projected on the user interface (310) to depict the action or inaction of turning on the source of light also known as the illumination module (316) for each of the peristaltic pumps (302, 303).

In FIG. 3, the peristaltic pump (302) is illuminated by the illumination module (316); in return, it has illuminated the illuminating medical infusion line (306). Comparing the illuminating signal to the non-illuminating signal: the peristaltic pump (303) receives a signal to not illuminate or receives no signal at all and the illumination module (316) remains un-light, forming the non-illuminated illuminating medical infusion line (308). Both the illuminated and non-illuminated illuminating medical infusion lines are interchangeable, and both possess the same capabilities. In the present embodiment, the difference is noted by the source of illumination, also known as the illumination module (316), receiving signal from the medical infusion pump (300) to turn on or off the source of illumination.

FIG. 3 also discloses the emergency indicator (304) as an assemblage on the medical infusion pump (300). The emergency indicator (304) can be audible or visual or both depending on the needs and usage of the medical infusion pump. Often times the emergency indicator (304) is a red blinking light accompanied by an audible cue originating from the medical infusion pump and alerting in certain repetitive time patterns until the issue is addressed.

An important aspect of the example embodiment in FIG. 3 is the infusion flow rate (314) and the infusion volume (312) indicators. In the smart pump system, these metrics can be associated with and programmed to the smart pump medical infusion pump to correspondingly take action on the illuminating medical infusion line. That is, the infusion flow rate can change the intensity of the light to grow stronger in brightness when the flow rate is higher and lower as the flow rate declines. Likewise, the infusion volume can cause intensity in the glow or cause the lights to blink at a rapid pace when the volume is high and lessen as the volume decreases. Many functions of illuminating can be tied to the smart pump in order to provide visual identification and cues to the medical practitioner to better understand the conditions of the medical fluid treatment.

Figure 4:
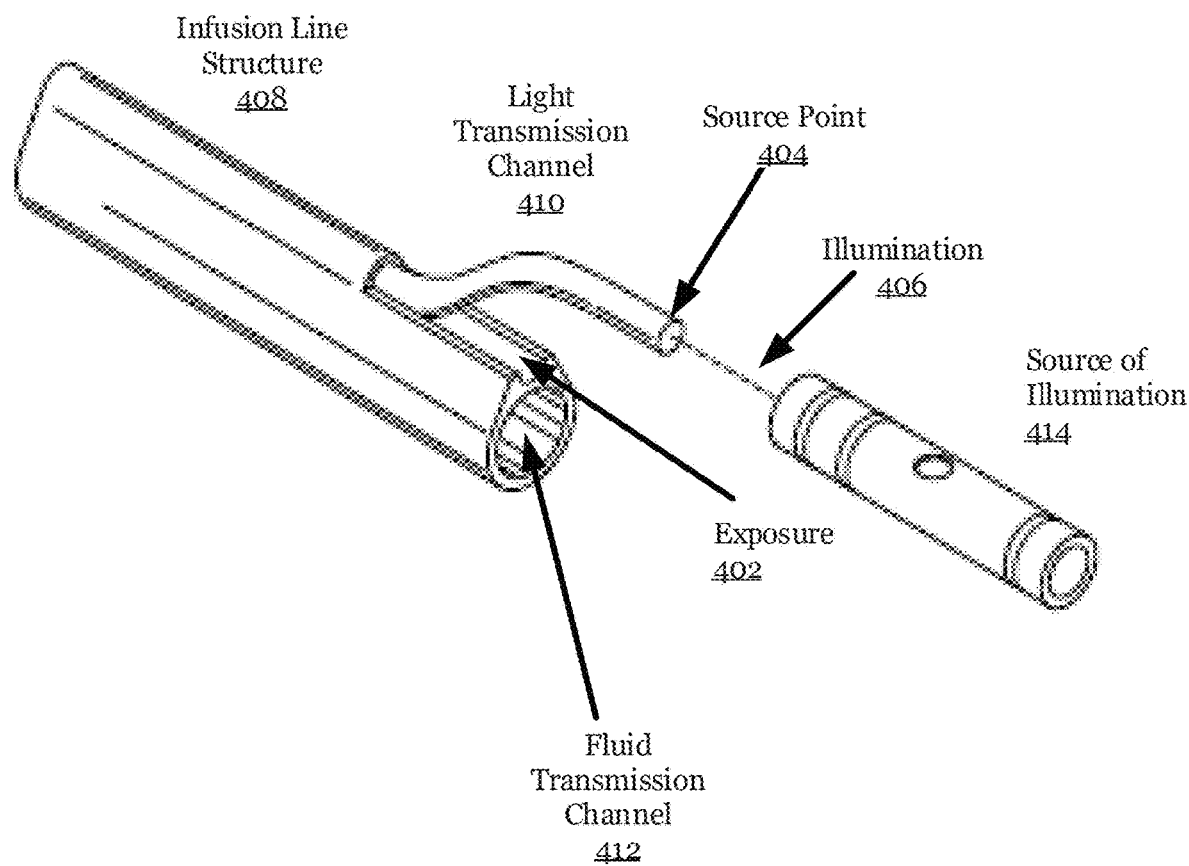
FIG. 4 is a schematic diagram of an illuminating medical infusion line as an additional embodiment of the present disclosure.

For further explanation, FIG. 4 discloses a schematic diagram of an illuminating medical infusion line (400) with the source of illumination (414) removed from the scope of the medical infusion pump. The example embodiment of FIG. 4 discloses the attachment of the fluid transmission channel (412) to the medical infusion pump as well as the light transmission channel (410) to the source of illumination (414), also referred to as the illumination module.

In the example embodiment of FIG. 4, the infusion line structure (408) is comprised of the light transmission channel (410) and the fluid transmission channel (412). Together the infusion line structure forms the illuminating medical infusion line (400). The infusion line structure is often a medical grade plastic or other resin that is inert to the medical fluids supplied through the transmission channels. Other types of composites and metals may be used to fashion the infusion line structure (408) so that it may safely transport medical fluids from a medical infusion pump to a medical patient.

Figure 5:
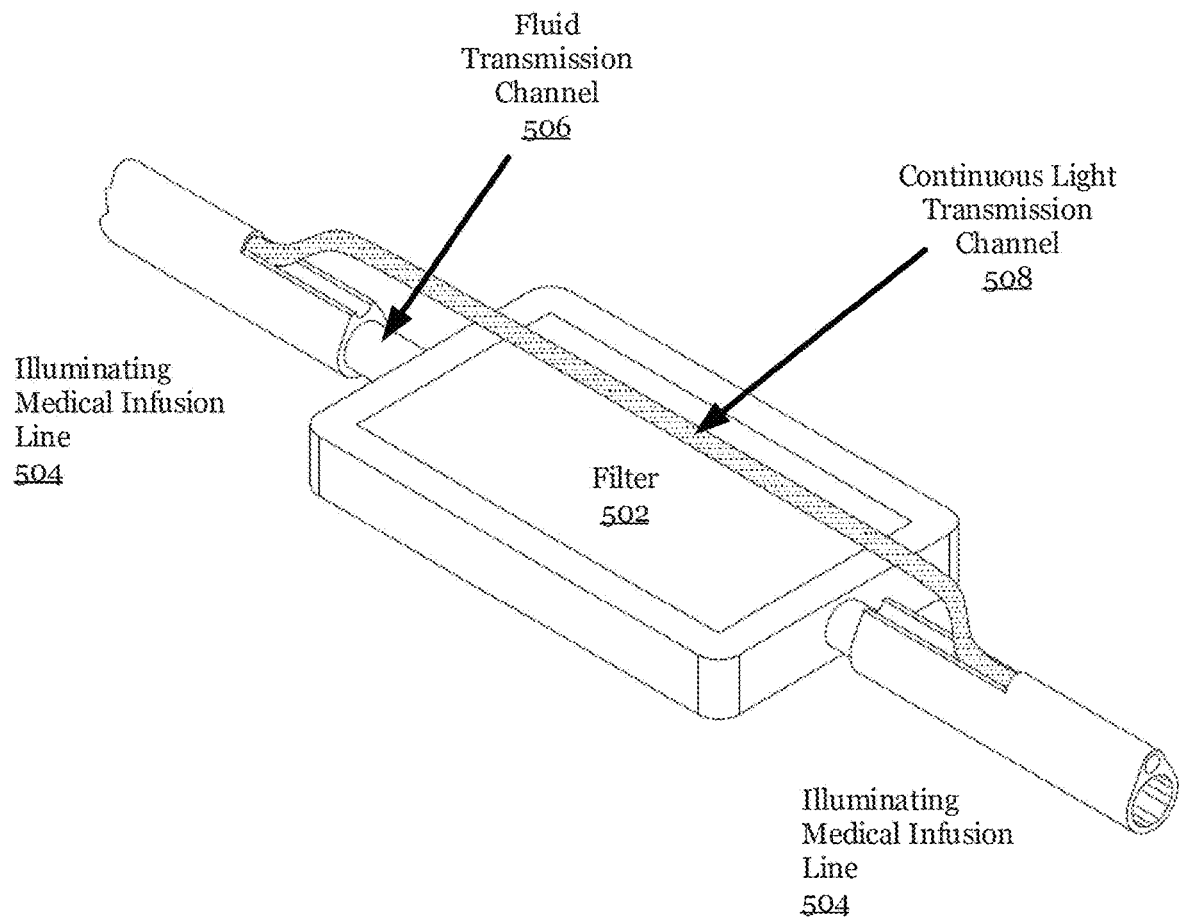
FIG. 5 is a schematic diagram of an illuminating medical infusion line with an inline component as an additional embodiment of the present disclosure.

As mentioned above with reference to FIG. 1, medical infusion often makes use of in-line components that may reside between the infusion pump, syringe or other origin of medical infusion and the patient receiving the infusion. Examples of such in-line components include filters, valves, access points, manifolds, and other in-line components as will occur to those of skill in the art. In FIG. 5, further explanation of how the illuminating medical infusion line (500) traverses an inline component is disclosed.

Figure 6:
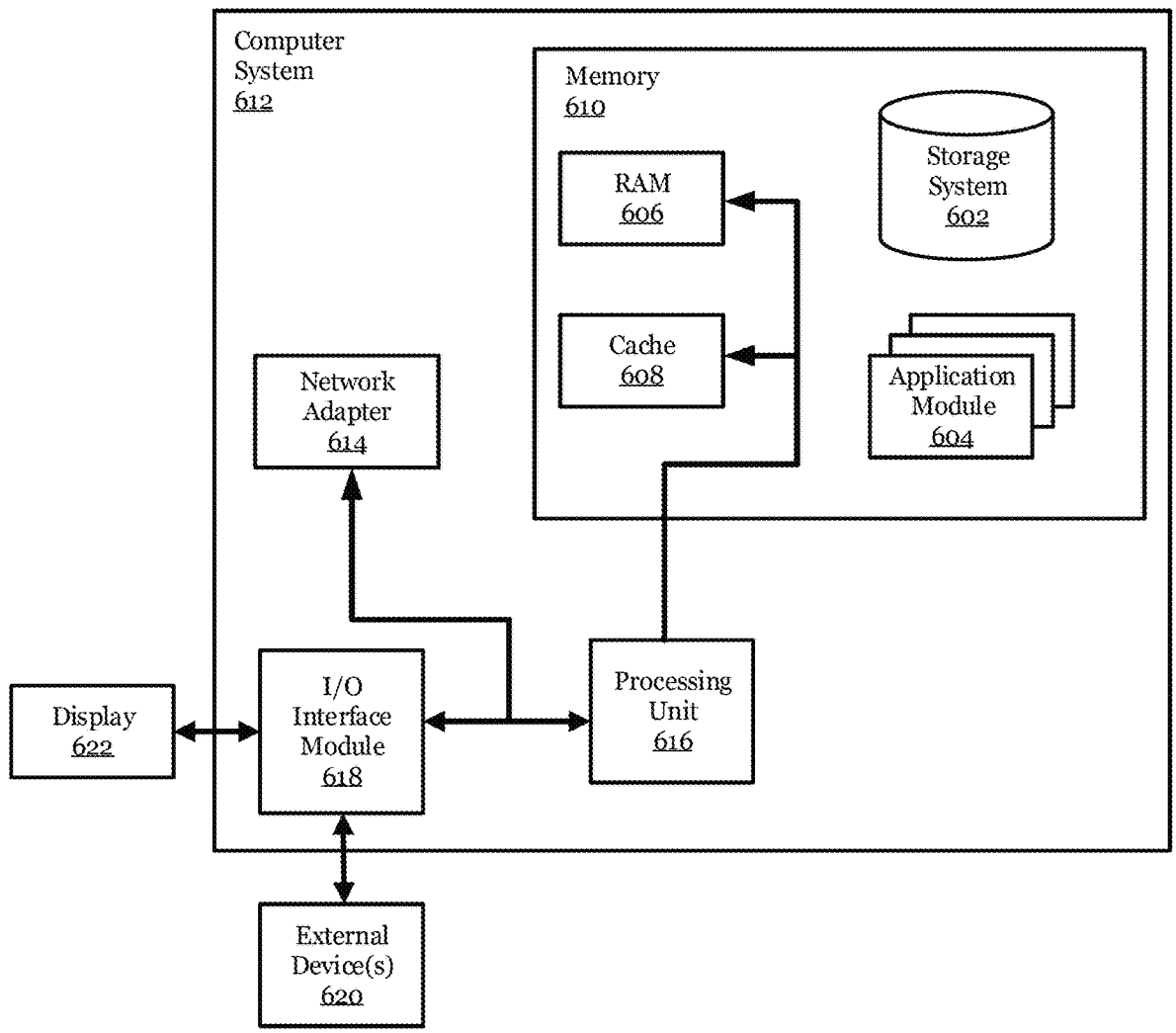
FIG. 6 is a component diagram of a computing device as an additional embodiment of the present disclosure.

FIG. 6 is a component diagram of an example embodiment of the computing device with the ability to process and execute instructions for a medical fluid treatment plan, medical diagnostic information, or general-purpose computing conditions for those in a medical facility. In the example embodiment of FIG. 6, the computer system (612) of the computing device (600) is comprised of several components. The computer system (612) contains a storage system (602) that is comprised of solid-state drive technology or may also be equipped with other hard drive technologies for storage of computing information. For example, the medical fluid treatment application may also reside in long term storage (602). The memory (610) of the example embodiment mobile computing system (612) also contains random access memory (606) which holds the program instructions along with a cache (608) for buffering the flow of instruction to the processing unit (616). Often times the executed medical fluid treatment application module (604) will reside in random access memory (606) as instructions are executed by the processing unit (616).

In the example embodiment of FIG. 6, the processing unit travels through a bus to the network adapter (614) that facilitates communications via network cards, wireless, Bluetooth®, and local area network adapters. The processing unit (616) is further configured through a bus to the input output interface module ('IO') (618). The IO module is connected to the display (622), which displays the GUI of the medical fluid treatment application. The IO module (618) is further configured to interface with many other external devices (620) such as universal serial bus adapters, lightning ports, power ports, and a whole host of additional IO devices that are traditionally found interfacing with a general-purpose and/or special purpose computing device. FIG. 6 is but one example embodiment of the configured computing device (600). Additional configurations and components of a general-purpose and special purpose computing device are disclosed herein.

Figure 7:
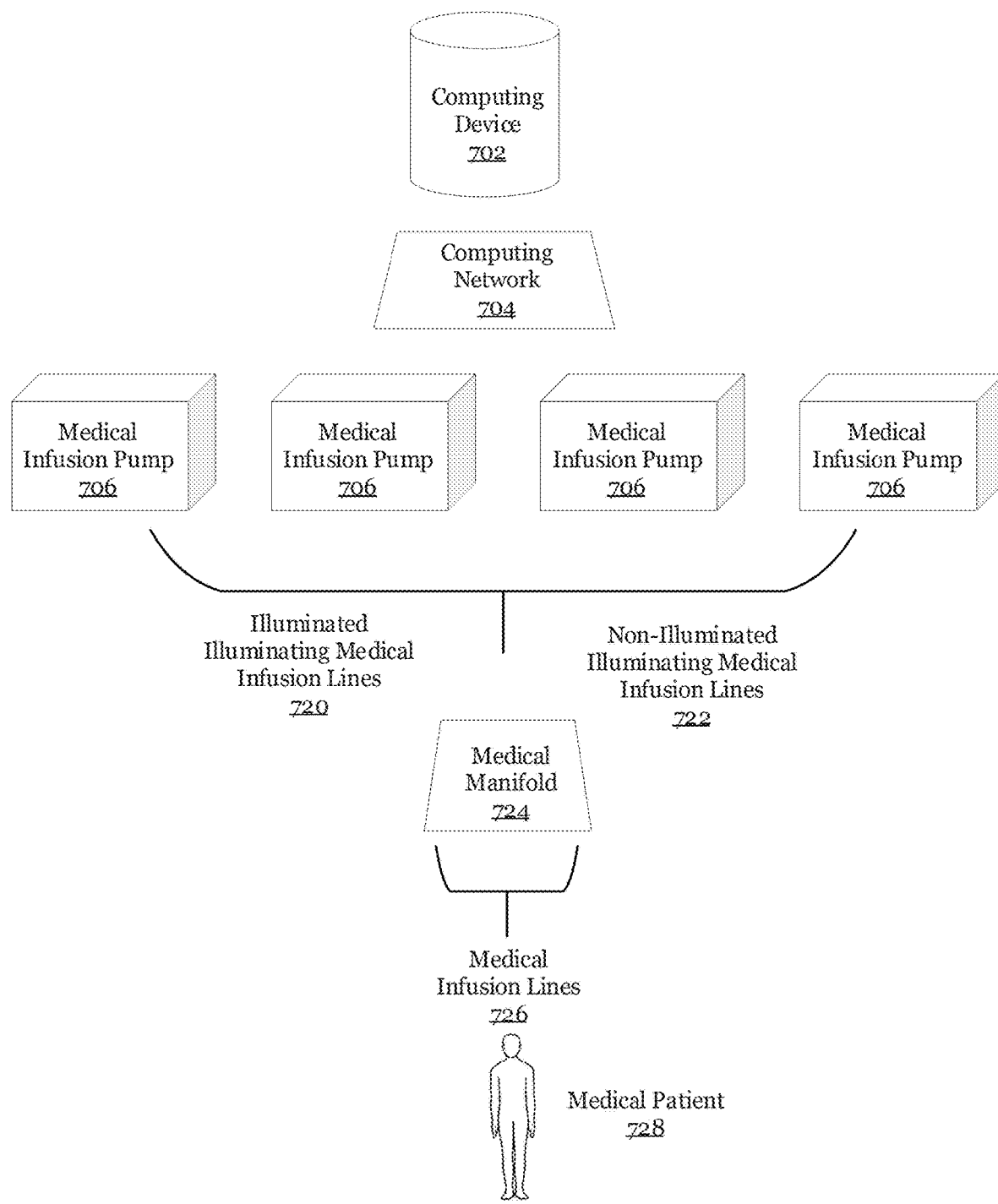
FIG. 7 is a block diagram of the system and method flow of a medical fluid treatment identification with an illuminated medical infusion line as an additional embodiment of the present disclosure.

For further explanation, FIG. 7 discloses a block diagram of the system and method flow of a medical fluid treatment identification with an illuminated medical infusion line as an example embodiment. As previously discussed, the computing device (702) can be a general purpose or special purpose computing device equipped with the technology capable of communicating with the medical infusion pumps (706). In the example embodiment, the computing device (702) transmits instructions or a signal through the computing network (704) to the plurality of medical infusion pumps (706). The medical infusion pumps (706) receive the signal or instructions from the computing device either through the computing network (704) or directly.

It is important to mention here that the computer network may be a cloud-based network and the resources connect to a cloud-based server to acquire the signal or instructions. Likewise, in additional disclosure, the computing network (704) is a local area network and is hard wired to the plurality of medical infusion pumps (706). Additionally, the hard-wired network is known to be beneficial in overcoming radio disturbance of wireless communications due to the equipment utilized in the medical field. It will be known to those of skill in the art the varying advantages and disadvantages of the respective computing networks.

The medical infusion pumps (706), after receiving a signal or instruction for a medical treatment plan, illuminate the corresponding illuminating medical infusion lines (720) while leaving those lines not specified to illuminate in an off state, also known as the non-illuminated illuminating medical infusion lines (722). The illumination of the illuminated medical infusion lines can be of varying color of light, as well as brightness, intensity, and even pattern-based lighting to symbolize different events in the medical fluid treatment plan or for diagnostic or other medical purposes. The overarching goal of the illuminated illuminating medical infusion lines is to reduce the cognitive load of the medical practitioner and aid in reducing medical error. Additional benefits such as diagnostic, equipment testing, informational, and educational are also contemplated in the disclosure.

In FIG. 7, the illuminated illuminating medical infusion lines (720) and the non-illuminated illuminating medical infusion lines (722) terminate into a medical manifold (724) wherein the medical manifold leads to additional medical infusion lines (726) that reach the medical patient (728). In additional embodiments, the illuminated illuminating medical infusion lines (720) and the non-illuminated illuminating medical infusion lines (722) terminate directly into the medical patient (728). It is also important to note that the illuminating medical infusion lines may also traverse inline medical components such as syringes, ports, filters, chambers, and other in line components typically found in medical fluid lines.

Figure 8:
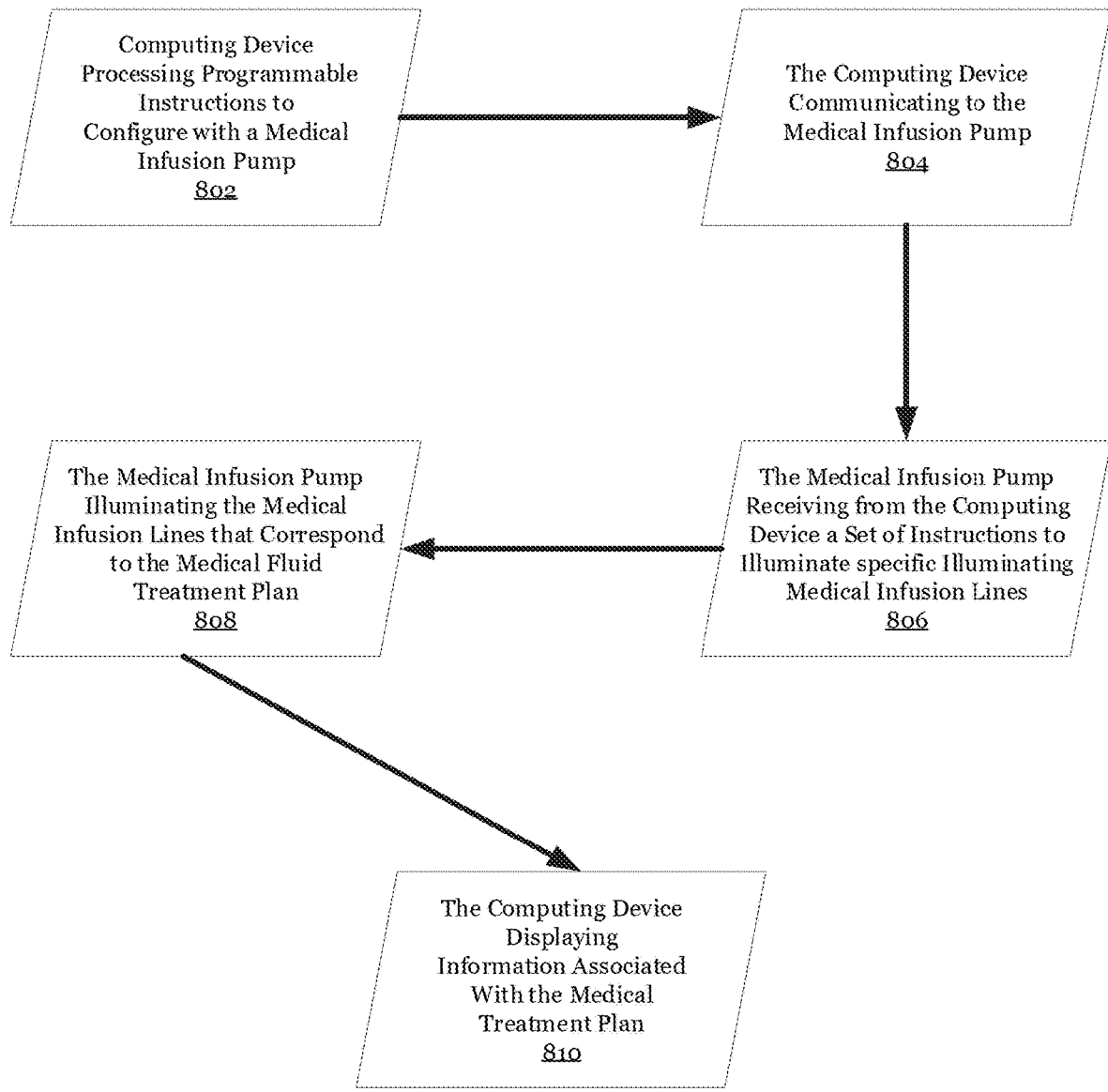
FIG. 8 is a flowchart of the method of medical fluid treatment utilizing illuminating medical infusion lines as an additional embodiment of the present disclosure.

For further explanation, FIG. 8 discloses an example embodiment flowchart of a method for medical fluid treatment utilizing illuminating medical infusion lines. A computing device processes the programmable instructions (802) from either a user or as a predefined operation in the medical treatment plan. The instructions include the corresponding medical infusion pump with which the computing device is configured to communicate with. The computing device then transmits or sends communications that include instructions or signals to the medical infusion pump (804). The medical infusion pump receives those communications (806) as signals or programmable instructions and interpret the communication to illuminate or not illuminate specific illuminating medical infusion lines. This illumination setting corresponds with the medical treatment plan, or the diagnostic plan, or educational objective of the user, or any additional purpose that would be known by those with skill in the art.

Continuing with FIG. 8, after the medical infusion pump receives the signal from the computing device, it illuminates the corresponding illuminating medical infusion lines (808) in accordance with the medical treatment plan. The computing device thereafter displays any results, signals, or interpretations from the medical fluid pump associated with the medical treatment plan. A result may simply be a verification that the light source is illuminated to the illuminating medical infusion line, or as simple as a verification that the signal was sent. A verification may be silent in nature and may only be observed by the programmable instructions. The purpose of the return diagnostic is to add continual improvements to the identification of medical fluid lines by bringing additional features to the interface to assist the user in interpreting the results as well as engaging with the system to improve human compute interaction.

Figure 9:
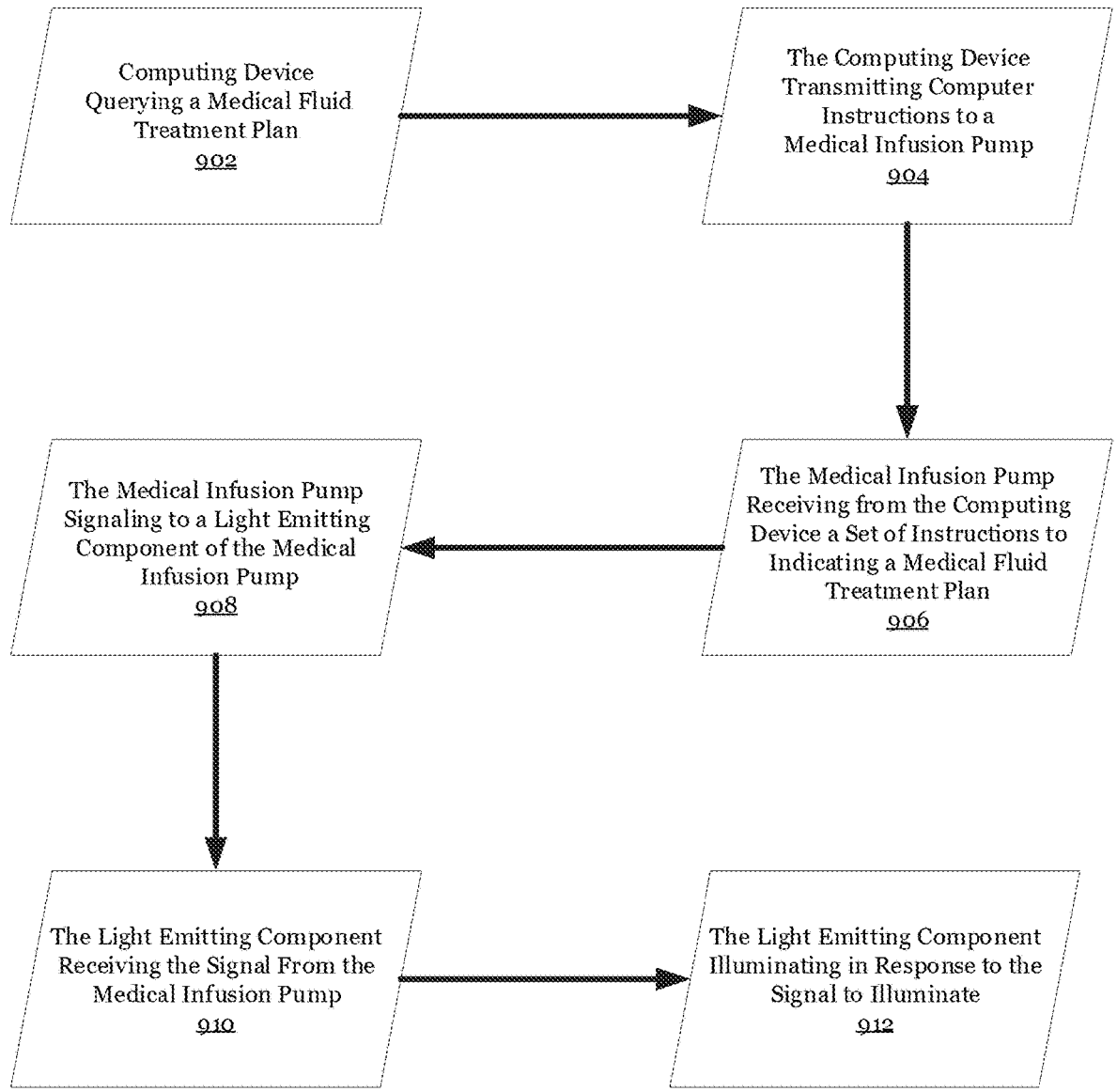
FIG. 9 is a flowchart of the method of medical fluid treatment utilizing illuminating medical infusion lines as an additional embodiment of the present disclosure.

For further explanation, the example embodiment of FIG. 9 is a flowchart of a method for medical fluid treatment utilizing illuminating medical fluid lines. In the example embodiment, the computing device queries (902) a medical treatment plan. By querying, the computing device locates a specific plan or receives instructions from the user of a medical fluid or diagnostic treatment plan. The computing device then transmits the queried instructions to the medical infusion pump (904) either through wireless or wired means. The medical infusion pump receives the set of instructions from the computing device (906) and interprets the instructions. The medical infusion pump then signals to the light emitting component of the medical infusion pump assembly (908). The light emitting module may be integrated within the medical infusion pump, added or installed after manufacture to an existing medical infusion pump, or assembled near or next to the medical infusion pump so as to be capable of forming contact with the illuminating medical infusion line.

In the example of FIG. 9, the light emitting component receives the signal form the medical infusion pump (910) and then the light emitting component illuminates (912) in response to the signal to illuminate from the medical fluid pump originating from the computing device. In additional embodiments, the light emitting component receives the signal from the computing device directly and is equipped with hardware and software to interpret the signal and produce the result of illuminating. Many interpretations and combinations of hardware and software as described herein can accomplish the task of transferring information and illuminating the illuminated medical infusion line. These different embodiments are non-limiting and differing combinations will be known from this disclosure.

Figure 10:
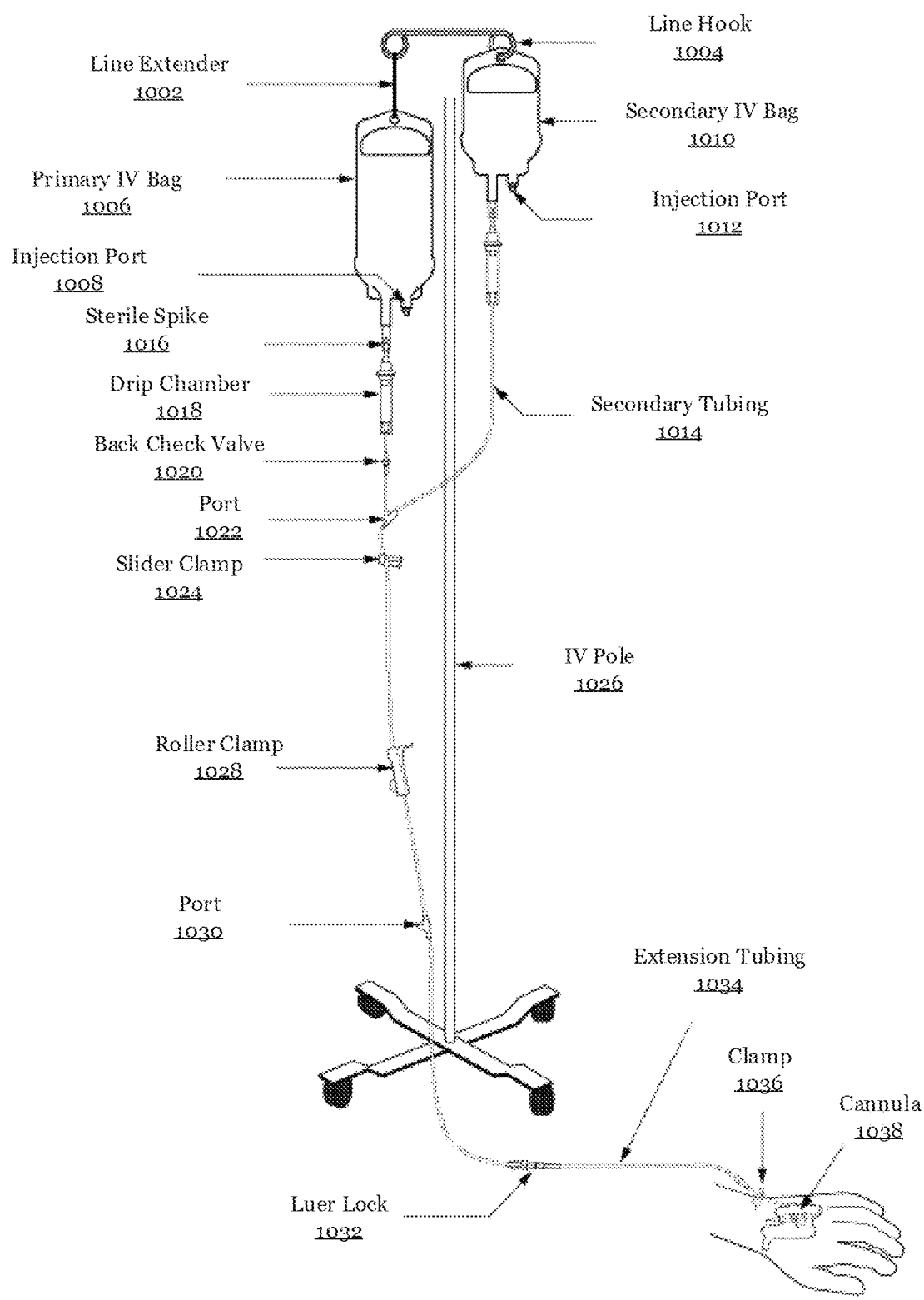
FIG. 10 is a schematic diagram of a standalone medical infusion line as an additional embodiment of the present disclosure.

For further explanation and clarification to components in a medical fluid treatment system, FIG. 10 is schematic diagram of a standalone medical infusion line. FIG. 10 serves to introduce the different components and is an example embodiment of many of the components that may be found in the present system. The line extender (1002) is a metal or sometimes plastic extender for lowering the primary IV bag (1006) height. Notably, the medical infusion pump is removed from this diagram for clarity in the components surrounding the medical infusion pump. The primary IV bag (1006) holds the primary IV medical fluid. The secondary IV Bag (1010) feeds into the primary IV tubing via the secondary tubing (1014). The variety of in line impediments are disclosed such as drip chamber (1018), back check valve (1020), port (1022), slider clamp (1024), and roller clamp (1028). The illuminated medical infusion line is capable of running continuous with the carious in line impediments and to provide identification of the line. The IV pole (1026) is synonymous with the IV rack in that both the IV pole and IV rack maintain holding the medical fluids. The Luer Lock® (1032) is a standardized fitting for medical fluid tubing and can be found throughout the different junctions of the illuminating medical fluid line. The extension tubing (1034) is medical tubing utilized to extend the reach of the tubing to the patient. The clamp (1036) clamps to the medical patient or near the medical patient that holds the medical fluid line in place. The cannula (1038) is a thin tube that can be inserted into the medical patient for the delivery of the medical fluids. The embodiments in FIG. 10 are additional embodiments to the present disclosure and do not serve as limiting factors. There may exist any number of the components within FIG. 10 applied to the other embodiments.

Figure 11:
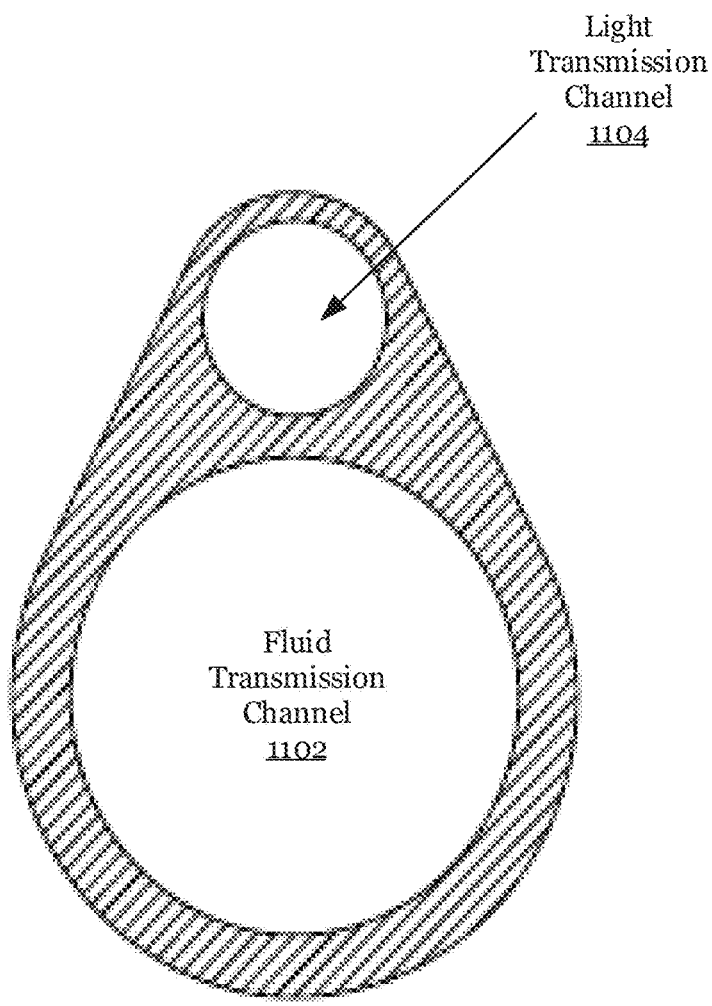
FIG. 11 is a cross section schematic of an illuminating medical infusion line as an additional embodiment of the present disclosure.

FIG. 11 is an example embodiment of a cross section of the illuminating medical infusion line (1100). Those of skill in the art will recognize that illuminating an infusion line provides increased aid to a medical practitioner tracing the line from the origin of the solution being administered through the infusion line to the patient. Those of skill in the art will also recognize that having the light transmission channel that illuminates the infusion line integrated with the fluid transmission line minimizes the risk of having a line identification system not attached to the infusion line itself which also provides increased aid to the medical practitioner in tracing the line and thereby provides increased safety to the patient.

The integration of light transmission channels and fluid transmission channels in illuminating infusion lines according to embodiments of the present invention may be implemented in a number of forms. In the example embodiment of FIG. 11, the fluid transmission channel (1102) is contiguous with a coextruded light transmission channel (1104) to form a single continuous illuminating medical infusion line (1100). Additional embodiments include the ability to affix the light transmission channel (1104) to the fluid transmission channel (1102) after forming the separate channels independently.

Figure 12:
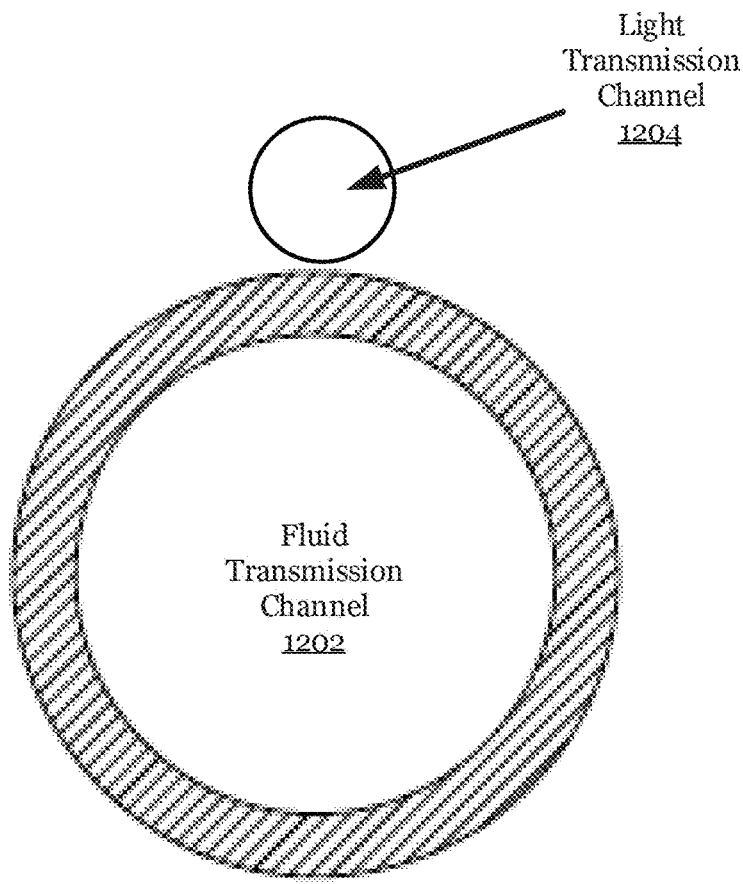
FIG. 12 is a cross section schematic of an illuminating medical infusion line as an additional embodiment of the present disclosure.

FIG. 12 is an example embodiment of a cross section of the illuminating medical infusion line (1200). In the example embodiment of FIG. 12, the light transmission channel (1204) is near the surface and following continuously along the fluid transmission channel (1202). This manufacturing process of the illuminating medical infusion line allows for attachment and manufacture thereof of separate channels for the light transmission channel (1204) and the fluid transmission channel (1202). Many benefits of this process will be apparent to those of skill in the art including the ability to retrofit current medical fluid lines with the technology of a light transmission channel to form the illuminating medical infusion line (1200).

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

Therefore, the following is claimed:

1. A system for administering a medical fluid treatment plan, comprising:
    a medical infusion pump, comprising:
        a power supply;
        a user interface;
        a pump with a fluid channel;
        an illumination module that produces light, wherein the illumination module is capable of varying the color of light, brightness of the light, and pattern of the light based on the medical fluid treatment plan;
        an emergency indicator;
    an illuminating medical infusion line, wherein the illuminating medical infusion line has a fluid transmission channel that is connected to the fluid channel of the pump on the medical infusion pump and a light transmission channel that is configured to receive the light from the illumination module of the medical infusion pump;
    a computing device, comprising:
        a network adapter configured to electronically communicate with the medical infusion pump;
        a software application executing on non-transitory memory of the computing device, the software application configured with a medical fluid treatment plan, wherein the medical fluid treatment plan is a set of medical fluids to be administered to a patient, and through the network adapter transmits the medical fluid treatment plan to the medical infusion pump where the user interface of the medical infusion pump displays the medical treatment plan and the illumination module illuminates the light transmission channel of the medical infusion line in respect to the medical fluid treatment plan; and
        a display, wherein the display projects the medical fluid treatment plan.

2. The system of claim 1, further comprising a cloud-based network, wherein the network adapter is configured to connect to the cloud-based network to communicate with the computing device and the medical infusion pump.

3. The system of claim 1, wherein the illumination module comprises at least a light emitting diode (LED).

4. The system of claim 1, wherein the illumination module comprises at least an organic light emitting diode (OLED).

5. The system of claim 1, further comprising the illumination module is equipped to vary color of light being emitted.

6. The system of claim 1, further comprising a source point on the illuminating light transmission channel for receiving the light from the illumination module.

7. An apparatus for administering and verifying a medical fluid treatment plan with illuminating infusion lines, comprising:
    a medical infusion pump, comprising:
        a housing;
        one or more pumps;

a computing device within the housing and in electrical communication with the one or more pumps;

a user interface in communication with the computing device, wherein the user interface displays a medical fluid treatment plan;

an emergency indicator on the housing;

an illumination module configured to receive a signal from the computing device to produce light; and a medical infusion line connected to the medical infusion pump, comprising:
- a fluid transmission channel in fluidic connection with a fluid within the one or more pumps of the medical infusion pump;
- a light transmission channel in optical connection through a source point with the illumination module of the medical infusion pump, wherein the illumination module is capable of varying color of the light, brightness of the light, and pattern of the light based on the medical fluid treatment plan.

8. The apparatus of claim 7, wherein the illumination module is equipped to vary intensity of light emitted from the illumination module as well as color of light being emitted from the illumination module.

9. The apparatus of claim 7, further comprising an audible indicator.

10. The apparatus of claim 7, wherein on the user interface further comprises an infusion flow rate field.

11. The apparatus of claim 7, wherein on the user interface further comprises an infusion volume field.

12. The apparatus of claim 7, wherein the illumination module is equipped to illuminate based on infusion flow rate, wherein a higher flow rate will illuminate the light transmission channel with more luminosity.

13. The apparatus of claim 7, wherein the illumination module is equipped to illuminate based on infusion volume, wherein as medical fluid is administered the light transmission channel will pulse or blink based on the infusion volume.

* * * * *